United States Patent
Fremy et al.

(10) Patent No.: US 11,643,673 B2
(45) Date of Patent: May 9, 2023

(54) FUNCTIONALISED CYCLIC DITHIOCARBAMATE SYNTHESIS METHOD

(71) Applicant: Arkema France, Colombes (FR)

(72) Inventors: Georges Fremy, Sauveterre de Bearn (FR); Arnaud Masselin, Saint Malo (FR)

(73) Assignee: Arkema France, Colombes (FR)

( * ) Notice: Subject to any disclaimer, the term of this patent is extended or adjusted under 35 U.S.C. 154(b) by 686 days.

(21) Appl. No.: 16/473,874

(22) PCT Filed: Dec. 21, 2017

(86) PCT No.: PCT/FR2017/053781
§ 371 (c)(1),
(2) Date: Jun. 26, 2019

(87) PCT Pub. No.: WO2018/122510
PCT Pub. Date: Jul. 5, 2018

(65) Prior Publication Data
US 2020/0149080 A1    May 14, 2020

(30) Foreign Application Priority Data

Dec. 29, 2016 (FR) ..................................... 16 63491

(51) Int. Cl.
*C07D 277/16* (2006.01)
*C07D 279/06* (2006.01)
*C12P 17/14* (2006.01)

(52) U.S. Cl.
CPC ............ *C12P 17/14* (2013.01); *C07D 277/16* (2013.01); *C07D 279/06* (2013.01)

(58) Field of Classification Search
CPC ...... C07D 277/16; C07D 279/06; C12P 17/14
See application file for complete search history.

(56) References Cited

U.S. PATENT DOCUMENTS

| | | | |
|---|---|---|---|
| 2,046,878 A | 7/1936 | Jones | |
| 3,960,861 A | 6/1976 | Reece et al. | |
| 9,365,877 B2 | 6/2016 | Fremy et al. | |

FOREIGN PATENT DOCUMENTS

| | | |
|---|---|---|
| CN | 103764832 A | 4/2014 |
| CN | 103804257 A | 5/2014 |
| CN | 103804258 A | 5/2014 |
| EP | 0323068 A2 | 7/1989 |
| WO | 2008013432 A1 | 1/2008 |
| WO | 2013029690 A1 | 3/2013 |

OTHER PUBLICATIONS

International Search Report and Written Opinion for International Application No. PCT/FR2017/053781, dated Mar. 26, 2018—7 pages.
Rabeh et al., "Structure and Mechanism of O-Acetylserine Sulfhydrylase", The Journal of Biological Chemistry, vol. 279, No. 26, Issue of Jun. 25, 2004—pp. 26803-26806.
Amarnath, V., et al., "Identification of a New Urinary Metabolite of Carbon Disulfide Using an Improved Method for the Determination of 2-Thioxothiazolidine-4-carboxylic Acid," 2001, pp. 1277-1283. vol. 14(9). Chemical Research in Toxicology.
Kopecky, J., et al., "A simple preparation of pure 2-thiothiazolidine-4-carboxylic acid (TTCA) as a reference standard for carbon disulfide exposure tests," Institute of Hygiene and Epidemiology, Bull. Soc. Chim. Belg., vol. 93 (3), pp. 231-232 (1984).
Korean Notification of Reason for Refusal for Korean Application No. 10-201 9-7021266, dated Jan. 7, 2021, 8 pages.
Hassan, E.A., et al., "Dithiocarbamates as Precursors in Organic Chemistry; Synthesis and Uses," 2014, vol. 189, pp. 300-323, Phosphorus, Sulfur, and Silicon, XP002774216.
Dobson, A.J., et al., "(4R)-(−)-2-Thioxothiazolidine-4-carboxylic Acid (Raphanusamic Acid)," 1998, C54, pp. 1634-1637, Acta Crystallographica, XP002774215.
Huang, H.A., et al., "Synthesis of (R)-2-Thioxothiazolidine-4-carboxylio acid and its esters," CAPLUS, 1995, One page, XP-002774217.
Nagai, S., "Synthesis of O-acetylhomoserine", Academic Press, vol. 17, 1971—pp. 423-424.
Hase, T., "The Growth Inhibitors from a Few Plants", Rev. Latinoamer Quim, 1985, pp. 1-5, vol. 16(1).
Johnson, D.J. et al., "The Measurement of 2-Thiothiazolidine-4-carboxylic Acid as an Index of the in Vivo Release of $CS_2$ by Dithiocarbamates", Chem. Res. Toxicol, 1996, pp. 910-916, vol. 9(5).
Chinese Office Action for Chinese Application No. 201780081601. 1, dated Jun. 16, 2022, with translation, 19 pages.

*Primary Examiner* — Rebecca L Anderson
(74) *Attorney, Agent, or Firm* — RatnerPrestia

(57) ABSTRACT

Provided is a process for synthesizing a functionalized cyclic dithiocarbamate.

6 Claims, No Drawings

FUNCTIONALISED CYCLIC DITHIOCARBAMATE SYNTHESIS METHOD

CROSS-REFERENCE TO RELATED APPLICATIONS

This is the national phase of International Application No. PCT/FR2017/053781, filed Dec. 21, 2017, which claims priority to French Application No. 1663491, filed Dec. 29, 2016.

FIELD OF THE INVENTION

The invention relates to the field of cyclic dithiocarbamates and more specifically to a process for synthesizing cyclic dithiocarbamates, and more particularly functionalized cyclic dithiocarbamates.

BACKGROUND OF THE INVENTION

Dithiocarbamates are organic compounds which may be used as radical precursors, intermediates in organic synthesis, vulcanization agents, chelating agents or enzyme inhibitors. Their fields of application are varied and they may be included, for example, in the composition of fungicides, herbicides, pesticides or insecticides in the agricultural sector, and they may be used in the rubber industry or else in the pharmaceutical industry in the treatment of diseases such as cancer or HIV.

As a result of the multitude of applications of dithiocarbamates, various techniques exist for synthesizing these compounds.

Thus, the article by Entesar A. Hassan, "Dithiocarbamates as precursors in organic chemistry, synthesis and uses", *Phosphorus, Sulfur and Silicon*, vol. 189, (2014), pages 300-323, describes various processes for synthesizing dithiocarbamates. A disclosure is given, for example, of the synthesis of N,N-dialkyl dithiocarbamate by reaction of a dithiocarbamate salt with an alkyl halide or with a dialkyl phosphate, or by addition of electron-deficient olefins. Said article also describes the production of dithiocarbamates by acylation of amines with chlorodithioformate. The preparation of cyclic dithiocarbamates by reaction of disulfides with (i) 2-aminoethanol, 2-aminoethyl sulfate and a 2-aminoethyl halide, (ii) primary amines and 1,2-dibromoethane in the presence of a base, (iii) aziridines and (iv) 2-iminothiazolidines is also disclosed. Cyclic dithiocarbamates may also be prepared by cyclization of β-hydroxyalkyldithiocarbamates by treatment with mesyl chloride in pyridine, or alternatively by cyclization of 2-alkylaminomethanethiol with thiophosgene in the presence of a base.

Moreover, patent application CN 103804258 describes the synthesis of dithiocarbamates from carbamide and carbon disulfide and patent application CN 103804257 discloses the preparation of diethyldithiocarbamates also from carbamide and carbon disulfide.

As regards patent application U.S. Pat. No. 2,046,876, it describes the synthesis of N-diaryldithiocarbamates by addition of carbon disulfide to diarylamine derivatives.

It will be readily appreciated that, owing to the multitude of possible applications of dithiocarbamates, there is an ever-increasing need for novel dithiocarbamates, in particular for novel functionalized dithiocarbamates, most particularly for applications in polymerization (notably for optional grafting onto an organic support), for applications in devulcanization and the like, but also, and more specifically, for novel optically active dithiocarbamates for the very numerous applications in pharmaceuticals, biology and the like.

It will also be appreciated from the description of the synthetic methods that there is also a need for syntheses of dithiocarbamates with processes which can be described as durable, i.e. which can be performed with mild temperature and pressure conditions, in aqueous solution with pH values close to neutrality, and with starting materials of renewable origin, and which are more generally more environmentally friendly.

SUMMARY OF THE INVENTION

It has now been discovered that it is possible to meet the objectives defined above, totally or at least partly, by performing the process according to the invention and as described below. Other objectives still will become apparent in the continuation of the description of the present invention which follows.

Thus, and according to a first aspect, the present invention relates to a process for synthesizing a functionalized cyclic dithiocarbamate of formula (I):

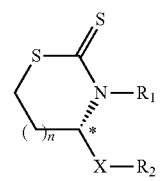

in which
  $R_1$ is a hydrogen or an aromatic or nonaromatic, linear or cyclic, saturated or unsaturated, branched or unbranched, hydrocarbon-based chain including from 1 to 20 carbon atoms, and which may include one or more heteroatoms chosen from O, S, N, P and Si;
  X represents —C(=O)— or —CH$_2$— or —CN;
  $R_2$ is (i) either nonexistent (when X represents —CN), (ii) or a hydrogen, (iii) or —OR$_3$, R$_3$ being a hydrogen or an aromatic or nonaromatic, linear or cyclic, saturated or unsaturated, branched or unbranched, hydrocarbon-based chain including from 1 to 20 carbon atoms, and which may comprise or more heteroatoms chosen from O, S, N, P and Si, (iv) or —NR$_4$R$_5$, with R$_4$ and R$_5$, which are or are not different, being a hydrogen or an aromatic or nonaromatic, linear or cyclic, saturated or unsaturated, branched or unbranched, hydrocarbon-based chain including from 1 to 20 carbon atoms, and which may include one or more heteroatoms chosen from O, S, N, P and Si;
  n is equal to 0, 1 or 2, preferably 1; and
  * represents an asymmetric carbon;
said process comprising the steps of:
a/ providing at least one compound of formula (II):

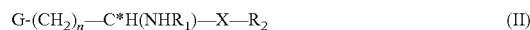

in which
  n, $R_1$, $R_2$, X and * are as defined previously,
  G represents either (i) R$_6$—C(=O)—O—CH$_2$—, or (ii) (R$_7$O)(R$_8$O)—P(=O)—O—CH$_2$—, or (iii) R$_7$O—SO$_2$—O—CH$_2$—;
  R$_6$ is a hydrogen or an aromatic or nonaromatic, linear or cyclic, saturated or unsaturated, branched or unbranched, hydrocarbon-based chain including from 1 to 20 carbon atoms, and which may include one or more heteroatoms chosen from O, S, N, P and Si;

$R_7$ and $R_8$, which may be identical or different, are chosen, independently of each other, from a proton H, an alkali metal, an alkaline-earth metal or an ammonium, preferably a proton H or an alkali metal and more particularly a proton H or Na;

b/ providing at least one inorganic trithiocarbonate;

c/ reaction between said at least compound of formula (II) and said at least inorganic trithiocarbonate in the presence of at least one enzyme chosen from sulfhydrylases, and preferably a sulfhydrylase associated with said compound of formula (II);

d/ production of at least one functionalized cyclic dithiocarbamate of formula (I);

e/ separation and isolation of said at least one functionalized cyclic dithiocarbamate of formula (I);

f/ optionally, additional functionalization of the functionalized cyclic dithiocarbamate of formula (I) obtained in step d/ or e/;

steps a/ and b/ optionally being performed simultaneously.

DETAILED DESCRIPTION OF THE INVENTION

It has been observed that the configuration of the asymmetric carbon is conserved throughout the reaction. As another advantage, it should be noted that the functionalized cyclic dithiocarbamate of formula (I) obtained according to the process according to the invention is an enantiomerically pure dithiocarbamate.

The term "functionalized cyclic dithiocarbamate" means any type of cyclic dithiocarbamate of formula (I), the nitrogen atom of which bears a functional group (except when $R_1$ represents a hydrogen atom) and/or the carbon atom of which as a to the nitrogen atom bears a functional group (except when —X— represents —$CH_2$— and when $R_2$ represents a hydrogen atom).

The invention will be understood more clearly in the light of the description and the examples which follow, but is not in any way limited to said examples.

According to one embodiment of the invention, $R_1$ represents the hydrogen atom.

According to another embodiment of the invention, —X— represents —C(=O)—.

According to yet another embodiment of the invention, $R_2$ represents —$OR_3$ with $R_3$ being the hydrogen atom.

According to another embodiment of the invention, n is equal to 0.

According to yet another embodiment of the invention, n is equal to 1.

According to a preferred embodiment of the invention, in formula (I), $R_1$ represents the hydrogen atom, —X— represents C(=O)—, $R_2$ represents —$OR_3$ with $R_3$ being a hydrogen, n is equal to 0, and the compound of formula (I) is L-raphanusamic acid.

According to another preferred embodiment of the invention, in formula (I), $R_1$ represents the hydrogen atom, —X— represents C(=O)—, $R_2$ represents —$OR_3$ with $R_3$ being the hydrogen atom, n is equal to 1, and the compound of formula (I) is L-homoraphanusamic acid.

According to a preferred embodiment of the invention, in formula (II), $R_1$ represents the hydrogen atom, —X— represents —C(=O)—, $R_2$ represents —$OR_3$ with $R_3$ being a hydrogen, n is equal to 0, and the compound of formula (II) is an L-serine derivative.

The L-serine derivative used in the process according to the invention may be chosen, for example and nonlimitingly, from O-phospho-L-serine, O-succinyl-L-serine, O-acetyl-L-serine, O-acetoacetyl-L-serine, O-propio-L-serine, O-coumaroyl-L-serine, O-malonyl-L-serine, O-hydroxymethylglutaryl-L-serine, O-pimelyl-L-serine and O-sulfato-L-serine.

Preferably, the L-serine derivative is chosen from O-phospho-L-serine, O-succinyl-L-serine, O-acetyl-L-serine and O-sulfato-L-serine.

Most particularly preferably, the L-serine derivative is O-acetyl-L-serine.

According to another preferred embodiment of the invention, in formula (II), $R_1$ represents the hydrogen atom, X represents the C=O function, $R_2$ represents $OR_3$ with $R_3$ being a hydrogen, n is equal to 1, and the compound of formula (II) is an L-homoserine derivative.

The L-homoserine derivative used in the process according to the invention may be chosen, for example and nonlimitingly, from O-phospho-L-homoserine, O-succinyl-L-homoserine, O-acetyl-L-homoserine, O-acetoacetyl-L-homoserine, O-propio-L-homoserine, O-coumaroyl-L-homoserine, O-malonyl-L-homoserine, O-hydroxymethyl-glutaryl-L-homoserine, O-pimelyl-L-homoserine and O-sulfato-L-homoserine.

Preferably, the L-homoserine derivative is chosen from O-phospho-L-homoserine, O-succinyl-L-homoserine, O-acetyl-L-homoserine and O-sulfato-L-homoserine.

Most particularly preferably, the L-homoserine derivative is O-acetyl-L-homoserine (OAHS).

The L-serine derivative and the L-homoserine derivative are either commercially available or obtained via any technique known to a person skilled in the art.

They may be obtained, for example, by fermentation of a renewable starting material. The renewable starting material may be chosen from glucose, sucrose, starch, molasses, glycerol and bioethanol, preferably glucose.

The L-serine derivative may also be produced from the acetylation of L-serine, the L-serine itself possibly being obtained by fermentation of a renewable starting material. The renewable starting material may be chosen from glucose, sucrose, starch, molasses, glycerol and bioethanol, preferably glucose.

The L-homoserine derivative may also be produced from the acetylation of L-homoserine, the L-homoserine itself possibly being obtained by fermentation of a renewable starting material. The renewable starting material may be chosen from glucose, sucrose, starch, molasses, glycerol and bioethanol, preferably glucose.

The inorganic trithiocarbonate used in the process according to the invention may be chosen from an alkali metal trithiocarbonate, an alkaline-earth metal trithiocarbonate and an ammonium trithiocarbonate.

Preferably, the inorganic trithiocarbonate is chosen from sodium trithiocarbonate, potassium trithiocarbonate, calcium trithiocarbonate and ammonium trithiocarbonate.

Particularly preferably, the inorganic trithiocarbonate is sodium trithiocarbonate.

During the process according to the invention, the reaction between said at least compound of formula (II) and said at least inorganic trithiocarbonate is performed in the presence of at least one enzyme, said enzyme preferably being a sulfhydrylase associated with said compound of formula (II).

Thus, when the compound of formula (II) is an L-serine derivative, the enzyme used may be chosen from O-phospho-L-serine sulfhydrylase, O-succinyl-L-serine sulfhydrylase, O-acetyl-L-serine sulfhydrylase, O-acetoacetyl-L-serine sulfhydrylase, O-propio-L-serine sulfhydrylase, O-coumaroyl-L-serine sulfhydrylase, O-malonyl-L-serine sulfhydrylase, O-hydroxymethylglutaryl-L-serine sulfhydrylase, O-pimelyl-L-serine sulfhydrylase and O-sulfato-L-serine sulfhydrylase.

Preferably, the enzyme associated with the L-serine derivative is chosen from O-phospho-L-serine sulfhydrylase, O-succinyl-L-serine sulfhydrylase, O-acetyl-L-serine sulfhydrylase and O-sulfato-L-serine sulfhydrylase.

Most particularly preferably, the enzyme associated with the L-serine derivative is O-acetyl-L-serine sulfhydrylase.

Moreover, when the compound of formula (II) is an L-homoserine derivative, the enzyme that is used may be chosen from O-phospho-L-homoserine sulfhydrylase, O-succinyl-L-homoserine sulfhydrylase, O-acetyl-L-homoserine sulfhydrylase, O-acetoacetyl-L-homoserine sulfhydrylase, O-propio-L-homoserine sulfhydrylase, O-coumaroyl-L-homoserine sulfhydrylase, O-malonyl-L-homoserine sulfhydrylase, O-hydroxymethylglutaryl-L-homoserine sulfhydrylase, O-pimelyl-L-homoserine sulfhydrylase and O-sulfato-L-homoserine sulfhydrylase.

Preferably, the enzyme associated with the L-homoserine derivative is chosen from O-phospho-L-homoserine sulfhydrylase, O-succinyl-L-homoserine sulfhydrylase, O-acetyl-L-homoserine sulfhydrylase and O-sulfato-L-homoserine sulfhydrylase.

Most particularly preferably, the enzyme associated with the L-homoserine derivative is O-acetyl-L-homoserine sulfhydrylase.

These said enzymes have optimum functioning, as is well known to those skilled in the art, when they are used in the presence of a cofactor, for instance pyridoxal 5'-phosphate (PLP).

The enzyme and its associated cofactor are generally dissolved in water before being added to the reaction medium. The proportion of enzyme, relative to the mass of the compound of formula (II), will be between 0.1% and 10% by weight, preferably between 1% and 5% by weight, and the amount of cofactor relative to the compound of formula (II) will be between 0.1% and 10% by weight, preferably between 0.5% and 5% by weight.

As regards the synthesis medium, temperature and pH conditions, reference may be made to those described in patent applications WO 2008/013432 and WO 2013/029690.

Thus, the reaction pH is preferably between 5 and 8, preferably between 6 and 7.5 and more particularly between 6.2 and 7.2. Said pH depends on the operating range of the enzyme and may be regulated according to the optimum for the enzyme, by adding basic trithiocarbonate or by adding dilute sulfuric acid or dilute ammonia. Preferably, the pH is adjusted by regulating the addition of basic trithiocarbonate.

Thus, the temperature during the reaction is between 10° C. and 45° C., preferably between 20° C. and 40° C. and more particularly between 25° C. and 35° C. Said temperature is chosen according to the operating range of the enzyme.

The reaction takes place in aqueous medium or in the presence of organic solvents, if these solvents are compatible with the enzymes used. Preferably, the reaction takes place in aqueous medium.

The reaction may be performed batchwise, semi-continuously or continuously. Any type of reactor known to a person skilled in the art may be suitable for reactions of this type.

According to one embodiment of the invention, the separation and isolation of the dithiocarbamate obtained may be performed according to any technique known to a person skilled in the art, in particular by precipitation and filtration.

The optional step f/ of the process according to the invention makes it possible to obtain additional functions which are different from those obtained after step d/ or in step e/.

This is because the functionalized cyclic dithiocarbamate of formula (I) obtained on conclusion of step d/ or on conclusion of step e/ may once again be functionalized during this step f/. For example, if X—R$_2$ represents a carboxylic function, said function can be esterified, reduced to an aldehyde, reduced to an alcohol and then etherified, amidated, nitrilated or the like. All the functions may be obtained according to techniques that are well known to a person skilled in the art, depending on the final use which is intended for the dithiocarbamate.

Thus, the functionalized cyclic dithiocarbamate of formula (I) obtained on conclusion of step d/ or e/ may be subjected to one or more additional chemical reactions in order to obtain one or more dithiocarbamates with different functions, said chemical reactions being all reactions that are known to a person skilled in the art.

According to one embodiment of the invention, an L-serine derivative such as O-acetyl-L-serine, an enzyme such as O-acetyl-L-serine sulfhydrylase, a cofactor such as pyridoxal 5'-phosphate (PLP) and basic trithiocarbonate, such as sodium trithiocarbonate, are placed in contact, it turns out, surprisingly, that one of the main products obtained is a cyclic dithiocarbamate corresponding to the name L-raphanusamic acid, raphanusamic acid being represented by the formula:

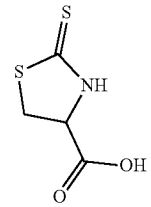

According to another embodiment of the invention, an L-homoserine derivative such as O-acetyl-L-homoserine, an enzyme such as O-acetyl-L-homoserine sulfhydrylase, a cofactor such as pyridoxal 5'-phosphate (PLP), and basic trithiocarbonate, such as sodium trithiocarbonate are placed in contact. It turns out, surprisingly, that one of the main products obtained is a cyclic dithiocarbamate corresponding to the name L-homoraphanusamic acid (cyclic higher homolog of L-raphanusamic acid), homoraphanusamic acid being represented by the formula:

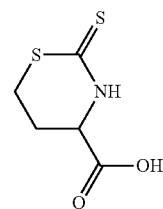

It has been observed that the synthesis of the dithiocarbamate may be accompanied by the production of a mercaptan of formula (III): HS—CH$_2$(CH$_2$)$_n$—C*H(NHR$_1$)—

X—R$_2$ in which n, R$_1$, R$_2$, X and * are as defined previously. This mercaptan may advantageously serve as a starting material for the synthesis of the dithiocarbamate by reaction with carbon disulfide in basic medium.

For example, in the case of the synthesis of homoraphanusamic acid, the mercaptan produced is homocysteine, which reacts with carbon disulfide according to the following scheme:

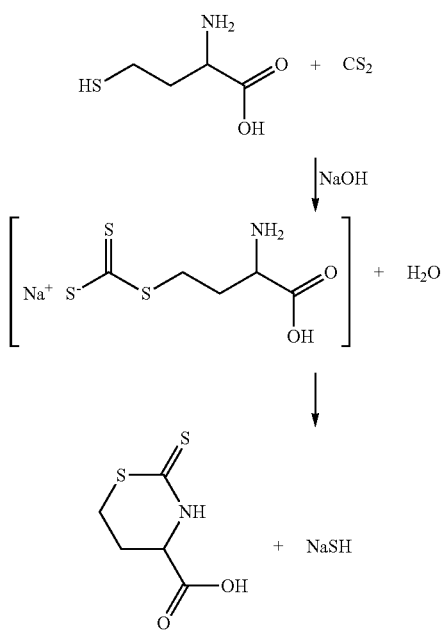

The compound in square brackets is an intermediate compound which appears in the course of the process. This compound, and also the other alkali metal, alkaline-earth metal or ammonium salts thereof, are novel and, in this respect, form part of the present invention. These compounds are referred to hereinbelow as "trithiocarbonates" ("sodium trithiocarbonate" in the case where the counterion is the sodium ion) of homocysteine.

More generally, the intermediate compound may be a compound of formula (IV):

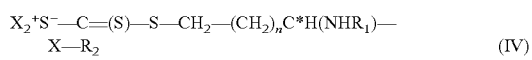

in which R$_1$, R$_2$, X, * and n are as defined previously and X$_2$ represents an alkali metal, an alkaline-earth metal or an ammonium group, preferably Na, K, NH$_4$ or Ca, more preferably Na.

According to another preferred embodiment of the invention, carbon disulfide may be added continuously or batchwise during the reaction.

The addition of carbon disulfide makes it possible notably to increase the dithiocarbamate synthetic yield.

According to a preferred embodiment of the invention, the L-serine derivative is O-acetyl-L-serine, the trithiocarbonate is sodium trithiocarbonate and the enzyme used is O-acetyl-L-serine sulfhydrylase.

According to a preferred embodiment of the invention, the functionalized cyclic dithiocarbamate of formula (I) obtained according to the process is L-raphanusamic acid.

According to another preferred embodiment of the invention, the L-homoserine derivative is O-acetyl-L-homoserine, the trithiocarbonate is sodium trithiocarbonate and the enzyme used is O-acetyl-L-homoserine sulfhydrylase.

According to a preferred embodiment of the invention, the functionalized cyclic dithiocarbamate of formula (I) obtained according to the process is L-homoraphanusamic acid.

As indicated previously, the configuration of the asymmetric carbon is conserved throughout the reaction. This makes it possible to obtain a particular enantiomer, which may be an advantage for certain applications, notably in the medical or pharmaceutical field.

Furthermore, the carboxylic acid present on the functionalized dithiocarbamate of formula (I) may make it possible to "attach" a wide diversity of compounds or molecules, enabling grafting onto an organic or inorganic support.

The functionalized cyclic dithiocarbamates of formula (I) prepared according to the process according to the invention may be used as radical precursors, intermediates in organic synthesis, vulcanization agents, chelating agents or enzyme inhibitors. Their fields of application are varied and they may be included, for example, in the composition of fungicides, herbicides, pesticides or insecticides in the agricultural sector, and they may be used in the rubber industry or else in the pharmaceutical industry in the treatment of diseases such as cancer or HIV.

EXAMPLES

Example 1: Enzymatic Synthesis of L-Homoraphanusamic Acid

Step 1:
O-Acetyl-L-homoserine (OAHS) was synthesized from L-homoserine and acetic anhydride according to Sadamu Nagai, "Synthesis of O-acetyl-L-homoserine", Academic Press (1971), vol. 17, pages 423-424.

Step 2:
10 g (62 mmol) of OAHS, synthesized beforehand, are placed in 140 ml of distilled water in a thermostatically controlled 250 mL glass reactor. The solution is brought to 35° C. with mechanical stirring. The pH of the reaction medium is 4.8. Before adding the enzyme, the pH is set at 6.5 with a few drops of sodium trithiocarbonate solution (4.78 g; 31 mmol, dissolved in 20 mL of distilled water). A sample of 1 mL of the reaction medium is taken (at t=0). A solution of pyridoxal 5'-phosphate (10 mmol, 0.4 g) and the enzyme O-acetyl-L-homoserine sulfhydrylase (0.6 g) are dissolved in 10 mL of water and then added to the reactor.

The reaction begins, which brings about a lowering of the pH. The reaction medium is maintained at a pH of 6.5 by slow addition of sodium trithiocarbonate via the dropping funnel. Samples (1 mL) are taken during the reaction. The analyses by potentiometric titration, TLC, HPLC and UPLC/UV-mass show a gradual disappearance of the reagents (OAHS and Na$_2$CS$_3$) and the gradual appearance, in increasingly large amounts, of the following compound:

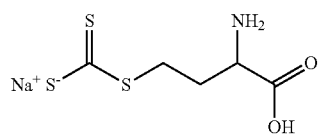

This intermediate compound in turn gradually disappears to give in equimolar amounts:

L-homoraphanusamic acid (the functionalized cyclic dithiocarbamate)

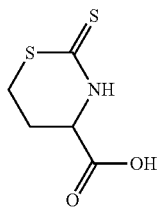

and L-homocysteine

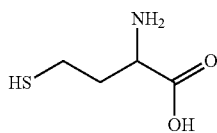

The only other products observed after the complete disappearance of the OAHS are traces of homoserine (hydrolysis of the OAHS).

Step 3: Separation and Isolation of the Dithiocarbamate:

The reaction medium is concentrated by partial evaporation of the water (so as to avoid the precipitation of the sodium acetate present in the reaction medium) under reduced pressure at 30° C. A precipitate forms since the dithiocarbamate proves to be the least soluble of the compounds present in the reaction medium. After filtration and drying, 4.9 g of dithiocarbamate are obtained. The overall isolated yield of dithiocarbamate is 45% (4.9 g obtained out of 11 g theoretically expected). Additional analyses on this dry product showed that this solid contains only traces of homocysteine.

Example 2: Synthesis of Dithiocarbamate (without Enzyme or Coenzyme)

Example 1 was repeated, the only difference being that the solution of pyridoxal 5'-phosphate (10 mmol; 0.4 g) and the enzyme O-acetyl-L-homoserine sulfhydrylase (0.6 g) dissolved in 10 mL of water were not added to the reactor. It turns out that the reaction does not start and that it is impossible to continually add the solution of trithiocarbonate while attempting to conserve a pH of 6.5. On increasing to pH 8 and then to pH 12 by addition of sodium trithiocarbonate solution, the only reaction observed is the start of hydrolysis of the OAHS to homoserine. This example shows that the synthesis of dithiocarbonate has to be catalyzed with an enzyme to be effective.

Example 3: Enzymatic Synthesis of Dithiocarbamate (with Addition of CS$_2$ at the End of the Reaction)

Step 1:

O-Acetyl-L-homoserine (OAHS) was synthesized from L-homoserine according to a protocol taken from the literature (Sadamu Nagai, "Synthesis of O-acetyl-l-homoserine", Academic Press (1971), vol. 17, pages 423-424).

Step 2:

10 g (62 mmol) of OAHS are placed in 140 mL of distilled water in a thermostatically controlled 250 mL glass reactor. The solution is brought to 35° C. with mechanical stirring. The pH of the reaction medium is 4.8. Before adding the enzyme, the pH is set at 6.5 by adding a few drops of sodium trithiocarbonate solution (the total amount added throughout the reaction is equal to 4.78 g, i.e. 31 mmol, dissolved in 20 mL of distilled water). A sample of 1 mL of the reaction medium is taken (at t=0).

A solution of 10 mL of distilled water containing 400 µL of a solution of pyridoxal 5'-phosphate (10 mmol/L) and of 0.6 g of enzyme (O-acetyl-L-homoserine sulfhydrylase) is prepared. A reduction in the pH indicating the formation of acetic acid makes it possible to state that the reaction has begun. It is necessary to maintain the reaction medium at a pH equal to 6.5. To do this, the sodium trithiocarbonate solution is added slowly via the dropping funnel. Samples (1 mL) are taken during the reaction.

When the analyses by potentiometric titration indicate a 50% conversion of the OAHS to homocysteine, 1.87 mL of carbon disulfide (31 mmol) are added to the reaction medium. The pH of the reaction medium is adjusted to 10 with 1M sodium hydroxide solution. The reaction medium is then brought to 50° C. Disappearance of the cysteine by potentiometric analysis is observed. Hydrochloric acid solution (2N) is then used to lower to 5 the pH of the reaction medium.

The additional analyses by TLC, HPLC and UPLC/UV-mass show the formation of a main product, L-homoraphanusamic acid.

The only other products observed after the complete disappearance of the OAHS are traces of homoserine (hydrolysis of the OAHS) and also traces of homocysteine.

Step 3: Separation and Isolation of the Dithiocarbamate

The reaction medium is concentrated by partial evaporation of the water (so as to avoid the precipitation of the sodium acetate and of the other salts present in the reaction medium) under reduced pressure at 30° C. A precipitate thus forms since the dithiocarbamate proves to be the species that is the least soluble in water. After filtration and drying, 9.2 g of dithiocarbamate are obtained. The overall isolated yield of dithiocarbamate is 9.2 g out of the theoretical 11 g, i.e. 84%.

Example 4: Enzymatic Synthesis of the Dithiocarbamate (with Addition of CS$_2$ During the Reaction Step 1:

O-Acetyl-L-homoserine (OAHS) was synthesized from L-homoserine according to a protocol taken from the literature (source: Sadamu Nagai, "Synthesis of O-acetyl-homoserine", Academic Press, (1971), vol. 17, pages 423-424).

Step 2:

10 g (61 mmol) of OAHS, synthesized beforehand, are placed in 140 ml of distilled water in a thermostatically controlled 250 mL glass reactor. The solution is brought to 35° C. with mechanical stirring. The pH of the reaction medium is 4.8. Before adding the enzyme, the pH is set at 7.2 by adding a few drops of the solution of trithiocarbonate and of carbon disulfide (4.78 g of trithiocarbonate, 31 mmol, 1.87 mL of carbon disulfide; 31 mmol dissolved in 20 mL of distilled water).

A sample of 1 mL of the reaction medium is taken (at t=0). A solution of 10 mL of distilled water containing 400 µL of a solution of pyridoxal 5'-phosphate (10 mmol/L) and of 0.6 g of enzyme (O-acetyl-L-homoserine sulfhydrylase) is prepared. A reduction in the pH indicating the formation of acetic acid makes it possible to state that the reaction has begun. It is necessary to maintain the reaction medium at a pH equal to 7.2. To do this, the sodium trithiocarbonate solution is added slowly via the dropping funnel. Samples (1 mL) are taken during the reaction. The analyses by potentiometric titration, TLC, HPLC and UPLC/UV-mass (after derivatization) show a gradual disappearance of the reagents (OAHS and Na$_2$S$_3$) and the gradual appearance, in increasingly large amounts, of L-homoraphanusamic acid. When all of the OAHS has reacted, the pH of the medium is lowered to 5 using 2M hydrochloric acid solution.

L-homoraphanusamic acid (the dithiocarbamate) is obtained.

Derivatization for the UPLC/UV-mass method was performed via the same method described in Example 1.

The only other products observed after the complete disappearance of the OAHS are traces of homoserine (hydrolysis of the OAHS) and also traces of homocysteine.

Step 3: Separation and Isolation of the Dithiocarbamate

The reaction medium is concentrated by partial evaporation of the water (so as to avoid the precipitation of the sodium acetate and of the other salts present in the reaction medium) under reduced pressure at 30° C. A precipitate thus forms since the dithiocarbamate proves to be the species that is the least soluble in water. After filtration and drying, 8.3 g of dithiocarbamate are obtained. The overall isolated yield of dithiocarbamate is 8.3 g out of the theoretical 11 g, i.e. 75.4%.

The invention claimed is:

1. A process for synthesizing a functionalized cyclic dithiocarbamate of formula (I):

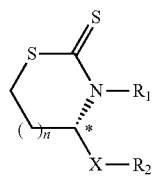

(I)

in which
R$_1$ is a hydrogen or an aromatic or nonaromatic, linear or cyclic, saturated or unsaturated, branched or unbranched, hydrocarbon-based chain including from 1 to 20 carbon atoms, and which may, optionally, include one or more heteroatoms chosen from O, S, N, P and Si;
X represents —C(=O)— or —CH$_2$— or —CN;
R$_2$ is (i) either nonexistent (when X represents —CN), (ii) or a hydrogen, (iii) or —OR$_3$, R$_3$ being a hydrogen or an aromatic or nonaromatic, linear or cyclic, saturated or unsaturated, branched or unbranched, hydrocarbon-based chain including from 1 to 20 carbon atoms, and which may, optionally, comprise or more heteroatoms chosen from O, S, N, P and Si, (iv) or —NR$_4$R$_5$, with R$_4$ and R$_5$, which are the same or different, being a hydrogen or an aromatic or nonaromatic, linear or cyclic, saturated or unsaturated, branched or unbranched, hydrocarbon-based chain including from 1 to 20 carbon atoms, and which may, optionally, include one or more heteroatoms chosen from O, S, N, P and Si;
n is equal to 0, 1 or 2; and
represents an asymmetric carbon;

said process comprising the steps of
a/ providing at least one compound of formula (II):

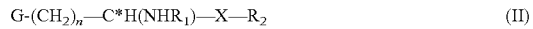

(II)

in which
n, R$_1$, R$_2$, X and * are as defined previously,
G represents either (i) R$_6$—C(=O)—O—CH$_2$—, or (ii) (R$_7$O)(R$_8$O)—P(=O)—O—CH$_2$—, or (iii) R$_7$O—SO$_2$—O—CH$_2$—;
R$_6$ is a hydrogen or an aromatic or nonaromatic, linear or cyclic, saturated or unsaturated, branched or unbranched, hydrocarbon-based chain including from 1 to 20 carbon atoms, and which may, optionally, include one or more heteroatoms chosen from O, S, N, P and Si;
R$_7$ and R$_8$, which may be identical or different, are chosen, independently of each other, from a proton H, an alkali metal, an alkaline-earth metal or an ammonium;
b/ providing at least one inorganic trithiocarbonate;
c/ reaction between said at least compound of formula (II) and said at least inorganic trithiocarbonate in the presence of at least one enzyme chosen from sulfhydrylases;
d/ production of at least one functionalized cyclic dithiocarbamate of formula (I);
e/ separation and isolation of said at least one functionalized cyclic dithiocarbamate of formula (I),
f/ optionally, additional functionalization of the functionalized cyclic dithiocarbamate of formula (I) obtained in step d/ or e/;
steps a/ and b/ optionally being performed simultaneously.

2. The process as claimed in claim 1, in which the functionalized cyclic dithiocarbamate of formula (I) is enantiomerically pure.

3. The process as claimed in claim 1, in which the functionalized cyclic dithiocarbamate of formula (I) is L-raphanusamic acid or L-homoraphanusamic acid.

4. The process as claimed in claim 1, in which the compound of formula (II) is chosen from O-phospho-L-serine, O-succinyl-L-serine, O-acetyl-L-serine, O-acetoacetyl-L-serine, O-propio-L-serine, O-coumaroyl-L-serine, O-malonyl-L-serine, O-hydroxymethylglutaryl-L-serine, O-pimelyl-L-serine, O-sulfato-L-serine, O-succinyl-L-homoserine, O-acetyl-L-homoserine, O-acetoacetyl-L-homoserine, propio-L-homoserine, O-coumaroyl-L-homoserine, O-malonyl-L-homoserine, O-hydroxymethylglutaryl-L-homoserine, O-pimelyl-L-homoserine, O-phospho-L-homoserine and O-sulfato-L-homoserine.

5. The process as claimed in claim 1, in which the sulfhydrylase is chosen from O-phospho-L-serine sulfhydrylase, O-succinyl-L-serine sulfhydrylase, O-acetyl-L-serine sulfhydrylase, O-acetoacetyl-L-serine sulfhydrylase, O-propio-L-serine sulfhydrylase, O-coumaroyl-L-serine sulfhydrylase, O-malonyl-L-serine sulfhydrylase, O-hydroxymethylglutaryl-L-serine sulfhydrylase, O-pimelyl-L-serine sulfhydrylase, O-sulfato-L-serine sulfhydrylase, O-phospho-L-homoserine sulfhydrylase, O-succinyl-L-homoserine sulfhydrylase, O-acetyl-L-homoserine sulfhydrylase, O-acetoacetyl-L-homoserine sulfhydrylase, O-propio-L-homoserine sulfhydrylase, O-coumaroyl-L-homoserine sulfhydrylase, O-malonyl-L-homoserine sulfhydrylase, O-hydroxymethylglutaryl-L-homoserine sulfhydrylase, O-pimelyl-L-homoserine sulfhydrylase and O-sulfato-L-homoserine sulfhydrylase.

6. The process as claimed in claim 1, in which the inorganic trithiocarbonate is chosen from an alkali metal trithiocarbonate, an alkaline-earth metal trithiocarbonate and an ammonium trithiocarbonate.

\* \* \* \* \*